US011145405B2

(12) United States Patent
Cheng et al.

(10) Patent No.: US 11,145,405 B2
(45) Date of Patent: Oct. 12, 2021

(54) METHODS AND DEVICES FOR GRADING A MEDICAL IMAGE

(71) Applicant: SHANGHAI UNITED IMAGING INTELLIGENCE CO., LTD., Shanghai (CN)

(72) Inventors: Jie-Zhi Cheng, Shanghai (CN); Zaiwen Gong, Shanghai (CN); Zhiqiang He, Shanghai (CN); Yiqiang Zhan, Shanghai (CN); Xiang Sean Zhou, Shanghai (CN)

(73) Assignee: Shanghai United Imaging Intelligence Co., Ltd., Shanghai (CN)

(*) Notice: Subject to any disclaimer, the term of this patent is extended or adjusted under 35 U.S.C. 154(b) by 0 days.

(21) Appl. No.: 16/509,950

(22) Filed: Jul. 12, 2019

(65) Prior Publication Data
US 2020/0211695 A1 Jul. 2, 2020

(30) Foreign Application Priority Data
Dec. 27, 2018 (CN) .......................... 201811610713.4

(51) Int. Cl.
G16H 30/40 (2018.01)
G16H 50/30 (2018.01)
G06N 3/08 (2006.01)
G06T 7/00 (2017.01)

(52) U.S. Cl.
CPC ............. G16H 30/40 (2018.01); G06N 3/084 (2013.01); G06T 7/0012 (2013.01); G16H 50/30 (2018.01); G06T 2207/10116 (2013.01); G06T 2207/20081 (2013.01); G06T 2207/20084 (2013.01); G06T 2207/30096 (2013.01)

(58) Field of Classification Search
CPC ........ G16H 30/40; G16H 50/30; G16H 50/20; G06N 3/084; G06T 7/0012; G06T 2207/10116; G06T 2207/20081; G06T 2207/20084; G06T 2207/30096; G06T 2207/30061; G06K 9/627
USPC .......................................... 382/132
See application file for complete search history.

(56) References Cited

U.S. PATENT DOCUMENTS 8,560,341 B2 10/2013 Iwase et al.
2007/0223807 A1 9/2007 Yankelevitz et al.
(Continued)

FOREIGN PATENT DOCUMENTS

CN 104732086 A 6/2015
CN 104840209 * 8/2015 ............. A61B 6/502
(Continued)

OTHER PUBLICATIONS

Chinese Patent Office, Office Action dated Dec. 3, 2019, in Application No. 201811610713.4.
(Continued)

Primary Examiner — Jerome Grant, II
(74) Attorney, Agent, or Firm — Faegre Drinker Biddle & Reath LLP

(57) ABSTRACT

Method and system for grading a medical image. For example, a system for grading a medical image comprising a grading network configured to provide a grading result corresponding to the medical image based on at least the medical image and/or a list of lesion candidates generated by a lesion identification network.

17 Claims, 8 Drawing Sheets

(56) References Cited

U.S. PATENT DOCUMENTS

| | | | | |
|---|---|---|---|---|
| 2015/0279106 | A1* | 10/2015 | Blanchflower | G06F 3/1462 345/2.2 |
| 2017/0061087 | A1 | 3/2017 | Boroczky et al. | |
| 2018/0232883 | A1 | 8/2018 | Sethi et al. | |
| 2020/0234815 | A1* | 7/2020 | Kozuka | G16H 50/70 |
| 2020/0335200 | A1* | 10/2020 | Takata | G16H 10/60 |
| 2020/0349394 | A1* | 11/2020 | Zhao | G06K 9/6271 |

FOREIGN PATENT DOCUMENTS

| | | | | |
|---|---|---|---|---|
| CN | 106372390 | A | 2/2017 | |
| CN | 107103187 | A | 8/2017 | |
| CN | 107247989 | A | 10/2017 | |
| CN | 107280697 | A | 10/2017 | |
| CN | 107330876 | A | 11/2017 | |
| CN | 107480721 | A | 12/2017 | |
| CN | 108257135 | A | 7/2018 | |
| CN | 108305671 | A | 7/2018 | |
| JP | 2009061174 | | * 3/2009 | A61B 6/03 |

OTHER PUBLICATIONS

Chinese Patent Office, Office Action dated Mar. 23, 2020, in Application No. 201811610713.4.

Chen, Introduction to Cognitive Computing, Section 18.5 (Image analysis in medical cognitive system), pp. 302-303, Apr. 2017.

Chinese Cancer Clinical Yearbook Editorial Board, Chinese Cancer Clinical Yearbook, pp. 135-139, Aug. 2007.

Chinese Patent Office, Office Action dated Jun. 23, 2020, in Application No. 201811610713.4.

Chinese Patent Office, Office Action dated Aug. 25, 2020, in Application No. 201811610713.4.

Chinese Patent Office, Office Action dated Nov. 3, 2020, in Application No. 201811610713.4.

Patent Cooperative Treaty, International Search Report dated Jan. 15, 2020, for PCT/CN2019/111556.

Patent Cooperative Treaty, Written Opinion dated Jan. 15, 2020, for PCT/CN2019/111556.

Chinese Patent Office, Office Action dated Jun. 4, 2021, in Application No. 201811610713.4.

* cited by examiner

METHODS AND DEVICES FOR GRADING A MEDICAL IMAGE

1. CROSS-REFERENCES TO RELATED APPLICATIONS

This application claims priority to Chinese Patent Application No. 201811610713.4, filed Dec. 27, 2018, incorporated by reference herein for all purposes.

2. BACKGROUND OF THE INVENTION

Certain embodiments of the present invention are directed to image processing. More particularly, some embodiments of the invention provide systems and methods for grading a medical image. Merely by way of example, some embodiments of the invention have been applied to diagnosing a medical image. But it would be recognized that the invention has a much broader range of applicability.

X-ray chest radiographs (or chest radiographs obtained in other methods) are commonly used in clinical examination. X-ray examinations (e.g., which generate chest radiographs) are often performed for general outpatient, emergency, and intensive care unit (ICU) to help diagnose and observe a patient's health. In physical examinations (e.g., as part of general health examinations or workforce entrance examinations), X-ray chest radiographs are also one of the standard examination items for checking whether there are any abnormal conditions in the chest of a subject (e.g., the patient). Therefore, the amount of X-ray chest radiographs produced each year is very large. As a result, the workload of reading X-ray chest radiographs in the radiology department is very large. In a typical physical examination session, most of the X-ray chest radiographs to-be-examined are normal, with the abnormal X-ray chest radiographs accounting for only a small portion of the total amount of the X-ray chest radiographs. As a result, the work of X-ray radiography diagnosis is relatively uneconomical in respect to the overall work of the radiology department. There is a need to improve the efficiency of clinical reading.

Triage is a method, process, or procedure for determining the priority of patients' treatments based on the severity and/or urgency of their condition. In some examples, the implementation of triage includes prompting a specialist, a doctor, a medical staff, or a medical team to take different measures according to the severity and/or urgency. For example, priority is given to treating the most critical patients, thereby maximizing the application efficiency of limited medical resources. The triage can be implemented in the emergency department, the treatment of wounded soldiers, and the telephonic consultations for pre-screening conditions. As the use of triage grow in popularity and demand in the radiology departments, such as for medical imaging and diagnosis, implementing triage in medical imaging applications has become increasingly important.

At present, conventional X-ray chest radiograph clinical workflow does not have prioritization functions (e.g., via an intelligent software), instead, the order of diagnostic analysis (or interpretation) is mostly performed in the order of first-in first-read. As such, concerns with the workflow is understandable due to the uneconomical and inefficient nature. For example, such concerning workflow is implemented in the physical examination applications described above. In the emergency application scenarios, although there are currently regulations requiring radiologists to diagnose and report on emergency medical images within 30 minutes. However, for some particularly urgent situations, such as during a shortage of radiologists in the middle of the night, the efficiency of the entire workflow has room for improvement. A specific application of the X chest radiograph severity classification method in an emergency scenario is, for example, the ability to prioritize cases of special emergency to the emergency department doctor or the corresponding doctor (e.g., the doctor on-staff), to allow the radiologist to quickly judge and reduce the waiting time (e.g., of up to 30 minutes). In the application scenario of the ICU, bedside chest X-rays are often used daily to observe the health status of critically ill patients, who may be in stable condition or in notable conditions. In emergency applications such as in the intensive care unit, grading (or classifying) of X-ray chest radiographs can help in identifying lung conditions, heart conditions, cardiovascular status, hilar conditions, bone tissue status, and/or pleural conditions. For example, a radiology doctor can first read and diagnose the urgent radiographs, and timely implement appropriate treatment improvements to help the patient.

In some scenarios, the intelligent application of classification of X-ray chest radiographs in the emergency clinical medical image diagnosis process, the applicable scenarios are very extensive, with clear need in the medical field for improved clinical work efficiency.

Conventional methods, however, are absent of such intelligent application products or solutions for X-ray chest radiographs diagnosis.

Therefore, there is a need for applying triage intelligent application for a wide variety of X-ray chest radiograph diagnosis procedures for identifying a wide range of chest conditions (e.g., lung condition, heart condition, cardiovascular condition, hilar condition, bone tissue condition, pleural condition, etc.) to improve the efficiency of workflows such as physical examination workflows in emergency services and intensive care units.

Technically, however, applying artificial intelligence technology to grading the severity and/or urgency of an image content of an X-ray chest radiograph is difficult. This may be due to the degree of urgency being closely related to the type of disease and the effects of abnormal phenomena, and the need to consider multiple diseases and multiple organs in the chest. As such, it is more complicated and difficult than applying artificial intelligence technology to diagnosing a single disease (e.g., lung nodules, breast lesions, or strokes). Specifically, for example, it is necessary to consider a plurality of diseases in the chest organ such as the lung and/or the heart, such as pulmonary effusion, emphysema, pneumothorax, cardiac hypertrophy, or the like, or multiple abnormal symptoms such as mediastinal thickening, aortic arch tortuosity, etc. Various other lung conditions, cardiac conditions, cardiovascular conditions, hilar conditions, bone tissue status, pleural conditions, etc., need to be considered to effectively implement the method of chest urgency emergency grading. Known conventional methods are not yet able to grade X-ray chest radiographs by severity and/or urgency.

3. BRIEF SUMMARY OF THE INVENTION

Certain embodiments of the present invention are directed to image processing. More particularly, some embodiments of the invention provide systems and methods for grading a medical image. Merely by way of example, some embodiments of the invention have been applied to diagnosing a medical image. But it would be recognized that the invention has a much broader range of applicability.

In various embodiments, a system for grading a medical image includes a grading network configured to provide a grading result corresponding to the medical image based on at least the medical image and/or a list of lesion candidates generated by a lesion identification network.

In some embodiments, the grading network is further configured to provide the grading result corresponding to the medical image based on at least the medical image and the list of lesion candidates generated by the lesion identification network.

In some embodiments, the grading network is further configured to provide the grading result corresponding to the medical image based on at least the medical image.

In some embodiments, the lesion identification network is configured to provide a score corresponding to the list of lesion candidates. In some examples, the grading result is provided further based on the score. In certain examples, the score is provided based on at least a probability value corresponding to the medical image including lesions of multiple lesion categories.

In some embodiments, the medical image includes a chest radiograph. In some examples, the list of lesion candidates includes at least one list selected from a group consisting of a list of lung lesion candidates, a list of cardiac lesion candidates, a list of cardiovascular lesion candidates, a list of hilar lesion candidates, a list of bone tissue lesion candidates, and a list of pleural lesion candidates.

In some embodiments, the grading network is further configured to provide one or more outputs to guide manual scheduling of a plurality of radiographs for manual review and diagnosis based on at least a plurality of grading results corresponding to the plurality of radiographs. In some examples, the grading network is further configured to automatically schedule the plurality of radiographs for manual review and diagnosis based on at least a plurality of grading results corresponding to the plurality of radiographs.

In some embodiments, the grading network is further configured to provide one or more outputs to guide manual scheduling of a plurality of radiographs for manual review and diagnosis based on at least a plurality of grading results corresponding to the plurality of radiographs, and automatically schedule the plurality of radiographs for manual review and diagnosis based on at least a plurality of grading results corresponding to the plurality of radiographs.

In some embodiments, the grading network is a student network trained by an attention transfer learning process includes: establishing a teacher network and the student network for the grading network; training the teacher network; and training the student network based on at least: extracting a feature map from one or more middle layers corresponding to both the student network and the teacher network; calculating one or more attention transfer learning losses corresponding to the one or more middle layers; and backpropagating the one or more attention transfer learning losses into the student network.

In some embodiments, the grading result corresponds to at least one selected from a group consisting of severity and urgency.

In some embodiments, the lesion identification network is configured to identify at least one lesion characteristic selected from a group consisting of color, shape, size, grayscale value, position, and morphology.

In some embodiments, the grading result is provided based on the medical image as a whole or one or more partial regions of the medical image.

In some embodiments, the grading result is selected from a group consisting of a first grade, a second grade, and a third grade, wherein: the first grade corresponds to a first priority for reading and diagnosis; the second grade corresponds to a second priority for reading and diagnosis; the third grade corresponds to a third priority for reading and diagnosis; the first priority being greater than the second and third priorities.

In various embodiments, a computer-implemented method for grading a medical image includes providing a grading result corresponding to the medical image based on at least the medical image and/or a list of lesion candidates generated by a lesion identification network.

In some embodiments, the computer-implemented method further includes providing the grading result corresponding to the medical image based on at least the medical image and the list of lesion candidates generated by the lesion identification network.

In some embodiments, the computer-implemented method further includes providing the grading result corresponding to the medical image based on at least the medical image.

In some embodiments, the computer-implemented method further includes providing a score corresponding to the list of lesion candidates using the lesion identification network. In some examples, the providing a grading result is further based on the score. In certain examples, the providing a score is based on at least a probability value corresponding to the medical image including lesions of multiple lesion categories.

In some embodiments, the computer-implemented method further includes providing one or more outputs to guide manual scheduling of a plurality of radiographs for manual review and diagnosis based on at least a plurality of grading results corresponding to the plurality of radiographs. In some examples, the computer-implemented method further includes automatically scheduling the plurality of radiographs for manual review and diagnosis based on at least a plurality of grading results corresponding to the plurality of radiographs.

In some embodiments, the computer-implemented method further includes training a student network to be the grading network based on an attention transfer learning process includes: establishing a teacher network and the student network for the grading network; training the teacher network; and training the student network based on at least: extracting a feature map from one or more middle layers corresponding to both the student network and the teacher network; calculating one or more attention transfer learning losses corresponding to the one or more middle layers; and backpropagating the one or more attention transfer learning losses into the student network.

In some embodiments, scheduling of the plurality of radiographs for manual review and diagnosis is based on at least one selected from a group consisting of expertise, pay level, and seniority.

In various embodiments, a non-transitory computer-readable medium with instructions stored thereon, that when executed by a processor, perform the process of: providing a grading result corresponding to the medical image based on at least the medical image and/or a list of lesion candidates generated by a lesion identification network.

4. BRIEF DESCRIPTION OF THE DRAWINGS

5. DETAILED DESCRIPTION OF THE INVENTION

Figure 1:
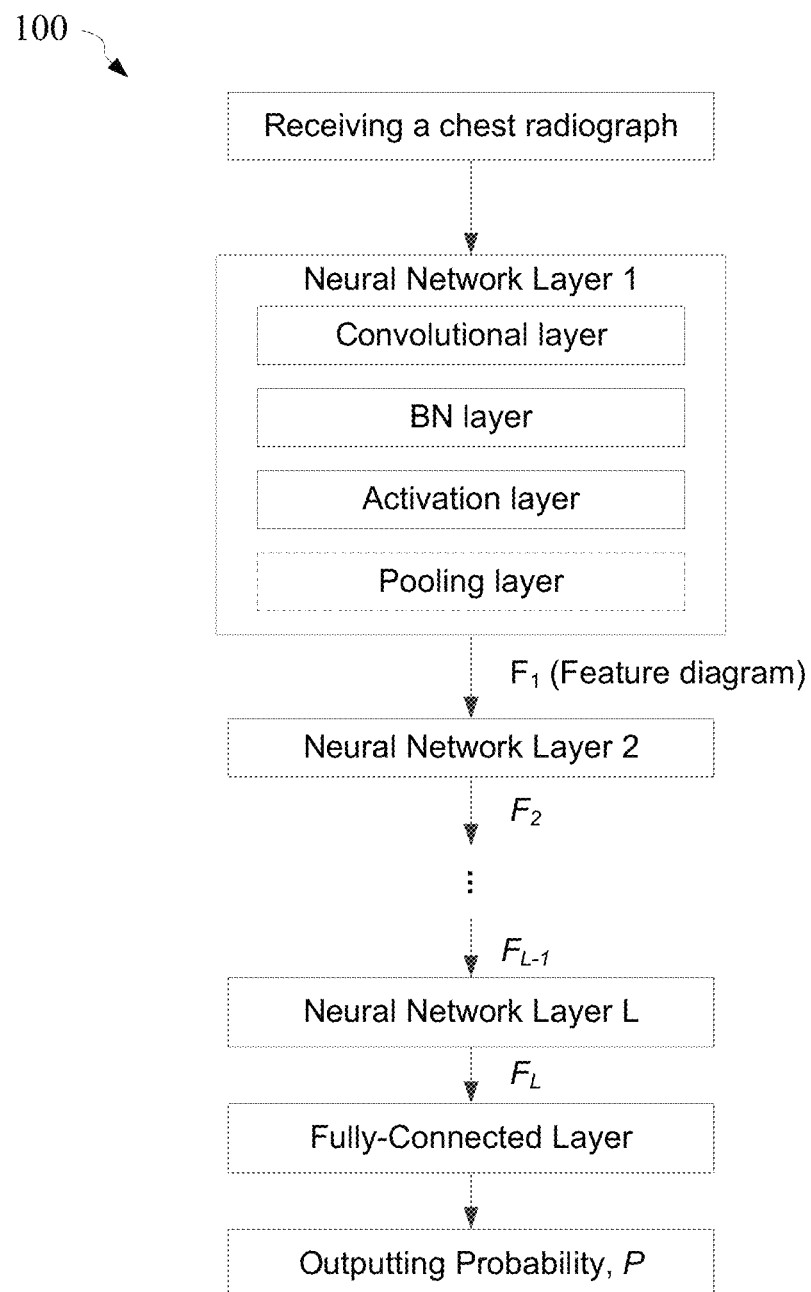
FIG. 1 is a simplified diagram showing a deep-learning neural network for grading an X-ray chest radiograph by severity and/or urgency, according to some embodiments of the present invention.

Certain embodiments of the present invention are directed to image processing. More particularly, some embodiments of the invention provide systems and methods for grading a medical image. Merely by way of example, some embodiments of the invention have been applied to diagnosing a medical image. But it would be recognized that the invention has a much broader range of applicability.

In some examples, the present disclosure relates to medical image assessment, and more particularly to the use of neural networks for smart medical image assessment.

In some examples, the present disclosure relates to a system for grading a medical image (e.g., by severity) including a grading (e.g., hierarchical) network configured to provide a grading (e.g., ranking) result at least based on an input medical image (e.g., that has been input into the system) and/or a list (e.g., listing) of lesion candidates generated by a lesion identification network. In certain embodiments, the present disclosure also relates to corresponding method and non-transitory computer-readable medium.

A grading network may be referred to as a hierarchical network. A neural network may be referred to as a network. A lesion identifying neural network may be referred to as a lesion recognizing neural network. A chest radiograph may be referred to as a film. An X-ray chest radiograph may be referred to as an X chest radiograph. Transfer learning may be referred to as migration learning. An identifying network may be referred to as an identification network. X-ray chest radiographs may be replaced by similar medical images, such as ones obtained by methods other than X-ray examination. Reading and diagnosis of a chest radiograph may be referred to as manual review and diagnosis of a chest radiograph.

In various embodiments, a system for grading a medical image includes a grading network configured to provide a grading result corresponding to the medical image based on at least the medical image and/or a list of lesion candidates generated by a lesion identification network.

In various examples, the lesion identification network is configured to provide a score corresponding to the list of lesion candidates. In some examples, the grading result is provided further based on the score. In some examples, the score is provided based on at least a probability value corresponding to the medical image including lesions of multiple lesion categories.

In various examples, the medical image includes a chest radiograph. In some examples, the list of lesion candidates includes one or more lists selected from a group consisting of a list of lung lesion candidates, a list of cardiac lesion candidates, a list of cardiovascular lesion candidates, a list of hilar lesion candidates, a list of bone tissue lesion candidates, and a list of pleural lesion candidates.

In various examples, the system for grading a medical image is configured to provide one or more prompts to guide manual scheduling of a plurality of radiographs for manual review and diagnosis based on at least a plurality of grading results corresponding to the plurality of radiographs. In some examples, the system for grading a medical image is configured to automatically schedule the plurality of radiographs for manual review and diagnosis based on at least a plurality of grading results corresponding to the plurality of radiographs.

In various examples, the grading network is trained by an attention transfer learning method. In some examples, training the grading network by the attention transfer learning method includes establishing a teacher network and a student network for the grading network, training the teacher network; and training the student network based on at least extracting a feature map from one or more middle layers corresponding to both the student network and the teacher network calculating one or more attention transfer learning losses corresponding to the one or more middle layers; and backpropagating the one or more attention transfer learning losses into the student network.

In various embodiments, a computer-implemented method for grading a medical image includes providing a grading result corresponding to the medical image based on at least the medical image and/or a list of lesion candidates generated by a lesion identification network.

In various examples, the computer-implemented method further includes providing a score corresponding to the list of lesion candidates using the lesion identification network. In some examples, the providing a grading result is further based on the score. In some examples, the providing a score is based on at least a probability value corresponding to the medical image including lesions of multiple lesion categories.

In various examples, the computer-implemented method further includes providing one or more prompts to guide manual scheduling of a plurality of radiographs for manual review and diagnosis based on at least a plurality of grading results corresponding to the plurality of radiographs. In some examples, the computer-implemented method further includes automatically scheduling the plurality of radiographs for manual review and diagnosis based on at least a plurality of grading results corresponding to the plurality of radiographs.

In various examples, the grading network is trained by an attention transfer learning method. In some examples, training the grading network by the attention transfer learning method includes establishing a teacher network and a student network for the grading network, training the teacher network, and training the student network based on at least extracting a feature map from one or more middle layers corresponding to both the student network and the teacher network, calculating one or more attention transfer learning losses corresponding to the one or more middle layers, and backpropagating the one or more attention transfer learning losses into the student network.

In various embodiments, a non-transitory computer-readable medium with instructions stored thereon, that when executed by a processor, perform the process of providing a grading result corresponding to the medical image based on at least the medical image and/or a list of lesion candidates generated by a lesion identification network.

In various embodiments, the disclosure relates to a system for grading a medical image including a grading network configured to provide one or more grading results based on at least one or more input medical images and/or a list of lesion candidates generated by a lesion identification network. The lesion identification network is part of the grading network or is a separate network from the grading network.

In various embodiments, the present disclosure relates to an artificial intelligence application for grading of one or more X-ray chest radiographs based on severity and/or urgency. In certain examples, the present disclosure systems and methods for identifying conditions, lesions, diseases, and the like in X-ray chest radiographs by using deep learning techniques, such as by providing grades and/or scores based on severity and/or urgency. In some examples, by using a deep learning neural network, the severity of an X-ray chest radiograph (which may be referred to as a film) can be graded, such as in a use case of a radiology department workflow. For example, the most severe chest radiographs can be placed at the top of a work list of the radiology department, followed by the less serious chest radiographs, and the likely-normal chest radiographs are placed later in the work list. In certain examples, the diagnosis of chest radiographs that are identified as likely-normal can be completed by appropriate division of labor and time, thereby improving the working efficiency of the clinical radiograph-analysis.

It should be understood that the described embodiments are only a part of the embodiments of the invention, and not all of the embodiments. All other embodiments obtained by those skilled in the art based on the embodiments of the present invention without creative efforts are within the scope of the present invention.

FIG. 1 is a simplified diagram showing a deep-learning neural network 100 for grading an X-ray chest radiograph by severity and/or urgency, according to some embodiments of the present invention. This diagram is merely an example, which should not unduly limit the scope of the claims. One of ordinary skill in the art would recognize many variations, alternatives, and modifications. In some examples, the neural network 100 includes a plurality of neural network layers including L amount of neural network layers and a fully-connected layer. In certain examples, the plurality of neural network layers includes a neural network layer 1 (first neural network layer), a neural network layer 2 (second neural network layer), and a neural network layer L ($L^{th}$ neural network layer). Although the above has been shown using a selected group of components for the neural network, there can be many alternatives, modifications, and variations. For example, some of the components may be expanded and/or combined. Other components may be inserted to those noted above. Depending upon the embodiment, the arrangement of components may be interchanged with others replaced.

In some embodiments, the neural network layer 1 includes a convolutional layer, a batch normalization (BN) layer, an activation layer, and optionally a pooling layer. In certain examples, one or more of the neural network layer 2 . . . the neural network layer L and the like also includes one or more of the convolutional layer, batch normalization (BN) layer, activation layer, and pooling layer described above. In certain embodiments, the neural network layer 1 is configured to receive an input image, which may be labeled as $F_0$. In some examples, the convolutional layer in the neural network layer 1 is configured to perform feature extraction on the input image $F_0$. In certain examples, the BN layer in the neural network layer 1 is configured to receive the feature(s) extracted by the convolutional layer and to normalize the output from the convolutional layer. In various examples, the activation layer in the neural network layer 1 is configured to receive the output (e.g., normalized) of the BN layer and apply an activation function to it to incorporate one or more nonlinear factors. In some embodiments, the pooling layer in the neural network layer 1 is configured to receive the output of the activation layer and to compress the feature(s). In various embodiments, the system 100 is configured to output the result after pooling or prior pooling of the neural network layer 1 as a first feature map (labeled as $F_1$). In some examples, the system 100 is configured to input the first feature map $F_1$ into the neural network layer 2. In certain embodiments, the convolutional layer, the BN layer, the activation layer, and/or the pooling layer in the neural network layer 2 is configured to process the first feature map $F_1$ and output a second feature map (labeled as $F_2$), wherein such process is repeated similarly for the remaining neural network layers in the plurality of neural network layers. As illustrated, the neural network layer L is configured to output a $L^{th}$ feature map (labeled $F_L$) to the fully connected layer. In some examples, the fully connected layer is configured to connect all the features and to output a probability value (labeled P). In various embodiments, the system 100 further includes a classifier (e.g., a soft-max layer) (not shown) is configured to receive the probability value P. In certain examples, the soft-max layer is configured as an output layer, such as a last layer of the neural network system 100, wherein the system 100 may be used for multi-classification (e.g., of lesion types in one or more organs). In various embodiments, the classification includes a single lesion classification and/or multiple lesion classifications. In some examples, more or less levels of neural network may be present in the neural network system 100. In various examples, the neural network is configured to be emulated via software by a general-purpose or specific-purpose hardware (e.g., circuitry).

In some embodiments, the neural network of the present disclosure for grading an X-ray chest radiograph by severity and/or urgency can be trained using deep learning methods, such as trained using multiple X-ray chest radiographs. In various embodiments, training the grading network 100 and/or a lesion identification network (e.g., as part of or separate from the grading network) is performed in a fully supervised or weakly supervised manner (e.g., selected based on the degree of completeness of data-labeling). For example, when the grading network is trained with training samples absence of sufficient annotated data, the training is conducted in a weakly supervised manner. In another example, when the grading network is trained with training samples with sufficiently (e.g., large amount or fully) annotated training samples (e.g., with clear and/or clean data), the training is conducted in a fully supervised manner.

In certain embodiments, the grading network 100 is configured to be trained using an attention transfer training method to improve the training of the deep convolutional neural network (e.g., the grading network 100), as there are increasing amount of new data and/or new lesion categories made available during training of the grading network 100. In certain examples, in the training of the deep convolutional neural network (e.g., the grading network 100), attention includes feature-based (e.g., color, shape, etc.) attention (FBA), spatial-based (e.g., position) attention, and/or the like. In some embodiments, using an attention transfer training method includes learning a source domain to solve a target domain. For example, classification of known lesions can be learned or transferred during training to enable classification of new lesions.

Figure 2:
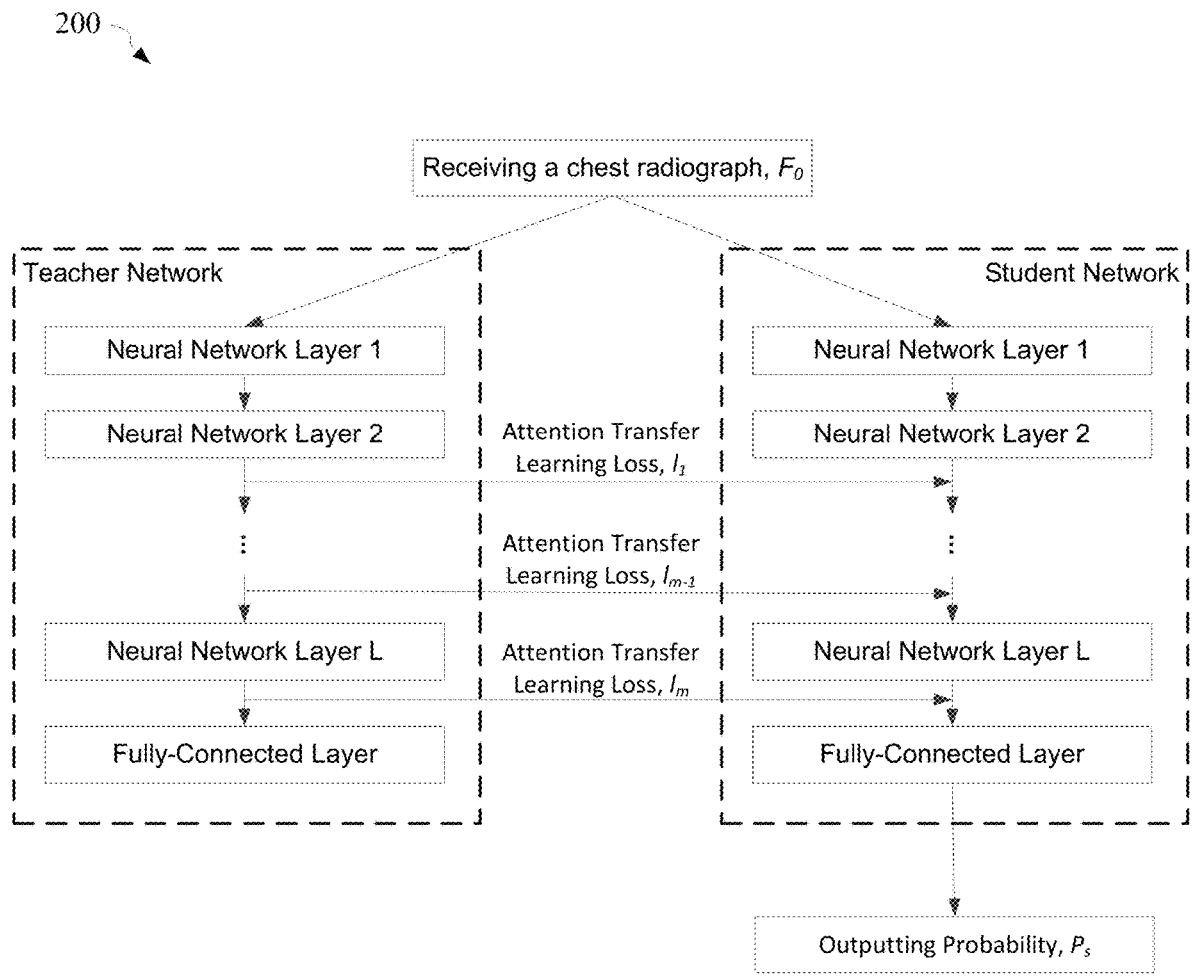
FIG. 2 is a simplified diagram showing a system for training a deep-learning neural network for grading an X-ray chest radiograph by severity and/or urgency, according to some embodiments of the present invention.

FIG. 2 is a simplified diagram showing a system 200 for training a deep-learning neural network for grading an X-ray chest radiograph by severity and/or urgency, according to some embodiments of the present invention. This diagram is merely an example, which should not unduly limit the scope of the claims. One of ordinary skill in the art would recognize many variations, alternatives, and modifications. In some examples, the system 200 includes a teacher network (a first network) and a student network (a second network). Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In various embodiments, the teacher network and/or the student network of the training system 200 includes a neural network structure similar to the structure of neural network 100 of FIG. 1. In some examples, the teacher network is a classification network for known lesions, and the student network is a classification network for new lesions. In certain embodiments, the teacher network is first trained. In various examples, the student network is next trained, wherein one or more feature maps of one or more middle (or intermediate) layers (e.g., neural network layers) corresponding to both the teacher network and the student network are extracted for calculating one or more corresponding transfer (migration) learning losses, and wherein the one or more transfer learning losses is back-propagated into the student network. In various examples, the system 200 is configured to calculate transfer learning loss $l_1$ based on the feature learning map $F_2$ from the feature map from the neural network layer 2 of the teacher network and input the transfer learning loss $l_1$ into the neural network layer 3 of the student network. Such calculation and input of transfer learning loss is repeated for the multiple neural network layers of the system 200. In certain embodiments, the transfer learning loss $l_m$ is calculated from the feature map $F_L$ output from the neural network layer L of the teacher network, and input into the fully connected layer of the student network. Finally, the trained student network is used for classifying a medical image, such as used for generating a grade based on severity and/or urgency. For example, for an input image $F_0$, the student network is configured to output a probability value $P_s$. In such teacher-student learning method, the teacher network's learned knowledge in the classification of known lesions can be transferred to the student network's ability classify new lesions.

Figure 3A:
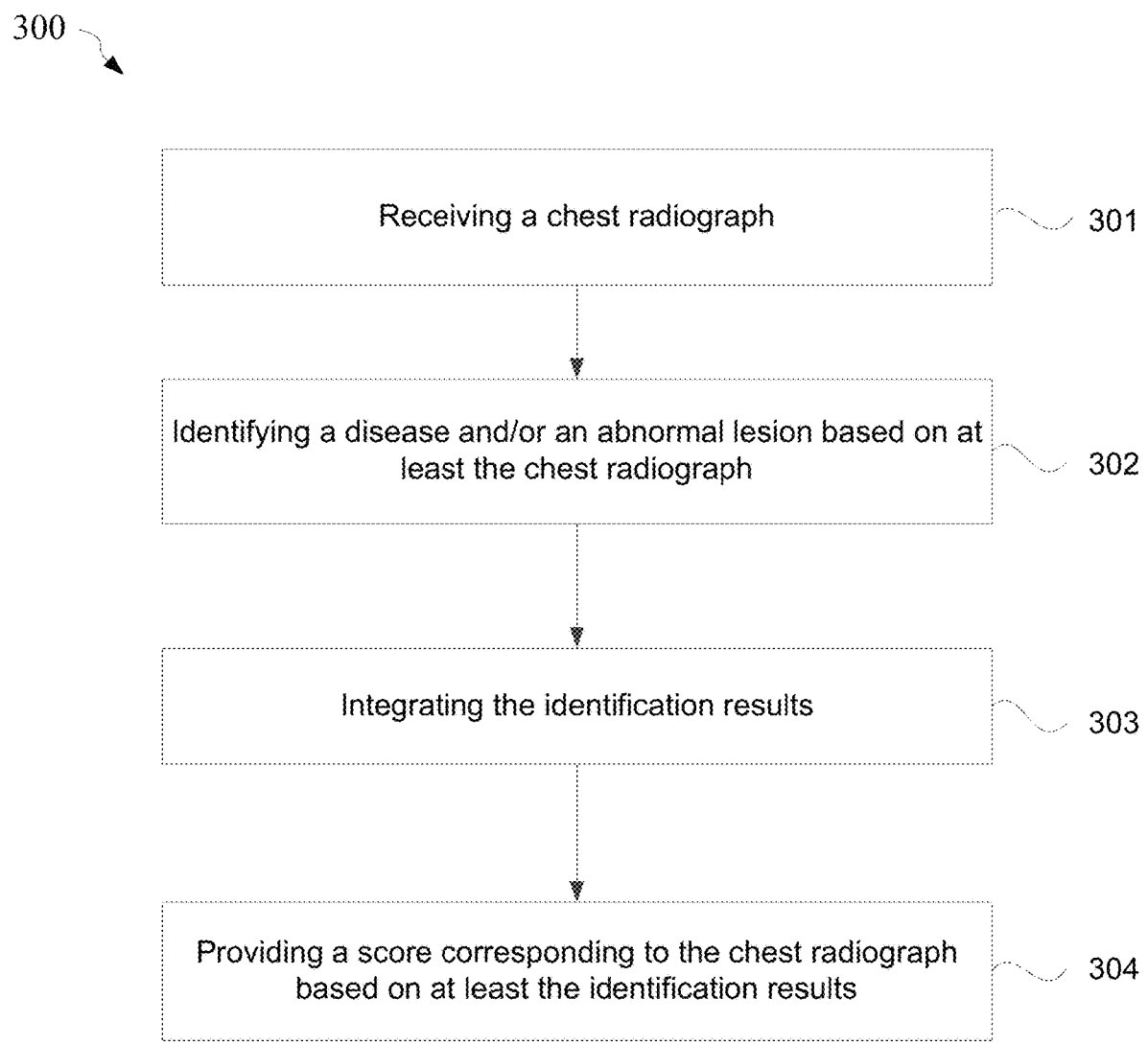
FIG. 3A is a simplified diagram showing a method for grading an X-ray chest radiograph by severity and/or urgency, according to some embodiments of the present invention.

FIG. 3A is a simplified diagram showing a method 300 for grading an X-ray chest radiograph by severity and/or urgency, according to some embodiments of the present invention. This diagram is merely an example, which should not unduly limit the scope of the claims. One of ordinary skill in the art would recognize many variations, alternatives, and modifications. In some examples, the method 300 includes a process 301 of receiving a chest radiograph, a process 302 of identifying a disease (one or more) and/or an (one or more) abnormal lesion based on at least the chest radiograph, a process 303 of integrating the identification results, and a process 304 of providing a score (e.g., based on severity and/or urgency) corresponding to the chest radiograph based on at least the identification results. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

Figure 3B:
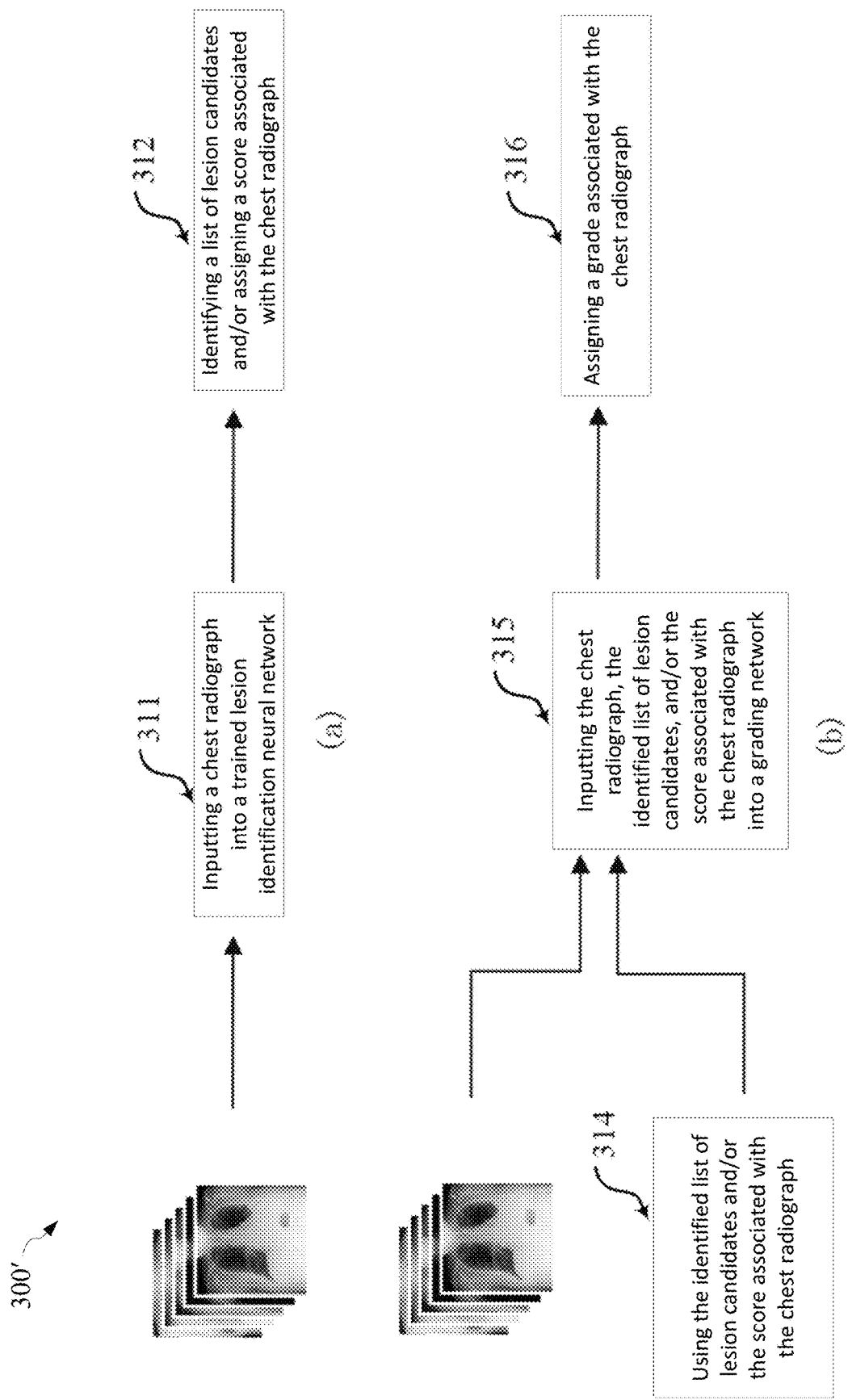
FIG. 3B is a simplified diagram showing a method for grading an X-ray chest radiograph by severity and/or urgency using artificial intelligence, according to some embodiments of the present invention.

FIG. 3B is a simplified diagram showing a method 300' for grading an X-ray chest radiograph by severity and/or urgency using artificial intelligence, according to some embodiments of the present invention. This diagram is merely an example, which should not unduly limit the scope of the claims. One of ordinary skill in the art would recognize many variations, alternatives, and modifications. In some examples, the method 300' includes an optional first leg of processes (a) including a process 311 of inputting a chest radiograph into a trained lesion identifying neural network, and a process 312 of identifying a list of lesion candidates and/or assigning a score associated with the chest radiograph, and a second leg of processes (b) including a process 314 of using the identified list of lesion candidates and/or the score associated with the chest radiograph, a process 315 of inputting the chest radiograph, the identified list of lesion candidates, and/or the score associated with the chest radiograph into a grading network, and a process 316 of assigning a grade (e.g., a label) associated with the chest radiograph. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various embodiments, implementation of the grading of an X-ray chest radiograph based on urgency and/or severity includes using a lesion identifying neural network and/or a grading (e.g., hierarchical) network. In some examples, the trained lesion identifying neural network is configured to identify one or more lesion candidates based on at least the chest radiograph. In certain examples, the trained lesion identifying neural network is configured to calculate, determine, and/or assign a score corresponding to the identified one or more lesion candidates, which can be represented as a list of lesion candidates. In various examples, the trained lesion identifying neural network is configured to extract one or more features or characteristics of each lesion candidate, such as color, shape, size, grayscale value, position, and/or morphology. In some embodiments, the trained lesion identifying neural network is deep learning-based. In certain embodiments, the trained lesion identifying neural network is configured to identify (or recognize), such as automatically, multiple diseases (or candidates of diseases) and/or multiple (abnormal) lesions (or candidates of lesions), such as concurrently. In some examples, assigning the score corresponding to the identified one or more lesion candidates includes assigning one or more scores each corresponding to one of the identified one or more lesion candidates. In certain embodiments, the lesion identifying neural network includes a soft-max layer configured to generate the score (assessment score) corresponding to a chest radiograph. For example, the soft-max layer is configured to output a N-dimensional vector, wherein a value of the $n^{th}$ dimension in the vector is the probability value that the chest radiograph belongs to a $n^{th}$ category (or classification) of a disease or lesion. In some examples, a process of providing a score (e.g., the process 304) corresponding to a chest radiograph includes providing a probability or probability value as the score (e.g., score equals to the probability). In certain examples, each dimension of the N-dimensions of the N-dimensional vector corresponds to a category of disease or lesion. In various embodiments, the soft-max layer is configured to map elements of the N-dimension vector $v_i$ to (0, 1), sum the mapped elements to a summed value of 1 to satisfy the probability property, and maintain the original order of the elements based on their original element sizes. In some embodiments, the soft-max layer is configured to output a classification target with a highest probability value corresponding to a mapped element, which the lesion identifying neural network, in some examples, is configured to consider the classification target as a primary lesion candidate among the identified one or more lesion candidates. In certain embodiments, the lesion recognition neural network is configured to automatically identify multiple lesions (e.g., different) on a medical image, with or without a feature extraction module configured to extract one or more features of a lesion.

In various embodiments, the trained lesion identification network is configured to output the list of lesion candidates and their corresponding scores for use as analysis results that are to be input into the grading network. In certain examples, the trained lesion identification network is configured to provide a score corresponding to the list of lesion candidates. In some examples, the score or grade assigned by the trained identification network and/or by the grading network is based on the type, the severity, the urgency, and/or the probability (or confidence level) of the lesion identified (e.g., by the trained lesion identification network). In various examples, the probability value indicates the probability of a lesion to be one of the lesion candidates included in the list of lesion candidates.

In some examples, the process 315 of inputting the chest radiograph, the identified list of lesion candidates, and/or the score(s) associated with the chest radiograph and/or the list of lesion candidates into the grading network is performed without inputting one or more of the chest radiograph, the identified list of lesion candidates, and the score(s) associated with the chest radiograph. In various examples, the trained network (e.g., including the trained lesion identifying neural network) is configured to grade, rank, label, and/or sort one or more chest radiographs, such as based on at least the analysis results of the lesion identifying neural network and/or the chest radiographs (as in the process 316). In an example, the trained network (e.g., including the trained lesion identifying neural network) is configured to grade, rank, label, and/or sort one or more chest radiographs based on at least the analysis results (e.g., a list of lesion candidates) of the lesion identifying neural network. In another example, the trained network (e.g., including the trained lesion identifying neural network) is configured to grade, rank, label, and/or sort one or more chest radiographs based on at least the chest radiographs. In certain examples, the grading network is configured to generate a grading result (e.g., a grade, a rank, a label) corresponding to the criticality, severity, and/or urgency of the chest radiograph as a whole or of one or more partial regions of the chest radiograph.

In some examples, the lesion identifying neural network and/or the grading network of FIG. 3A and/or FIG. 3B is the neural network 100 depicted in FIG. 1, and in certain examples, is trained by the system 200 depicted in FIG. 2. It is to be understood that other neural networks and/or systems and methods for training a neural network can also be used in various embodiments of the present disclosure.

In certain examples, the training (or learning) of the lesion identifying neural network and/or the grading network can be performed using cascaded learning method. In some embodiments using such cascaded learning method, the process of detecting image features (e.g., explicitly) is removed to achieve image-level severity and gradual grading. In some examples, the lesion identification network and the grading network can be implemented as a single (e.g., merged) network. For example, the grading network includes the lesion identification network.

Figure 4:
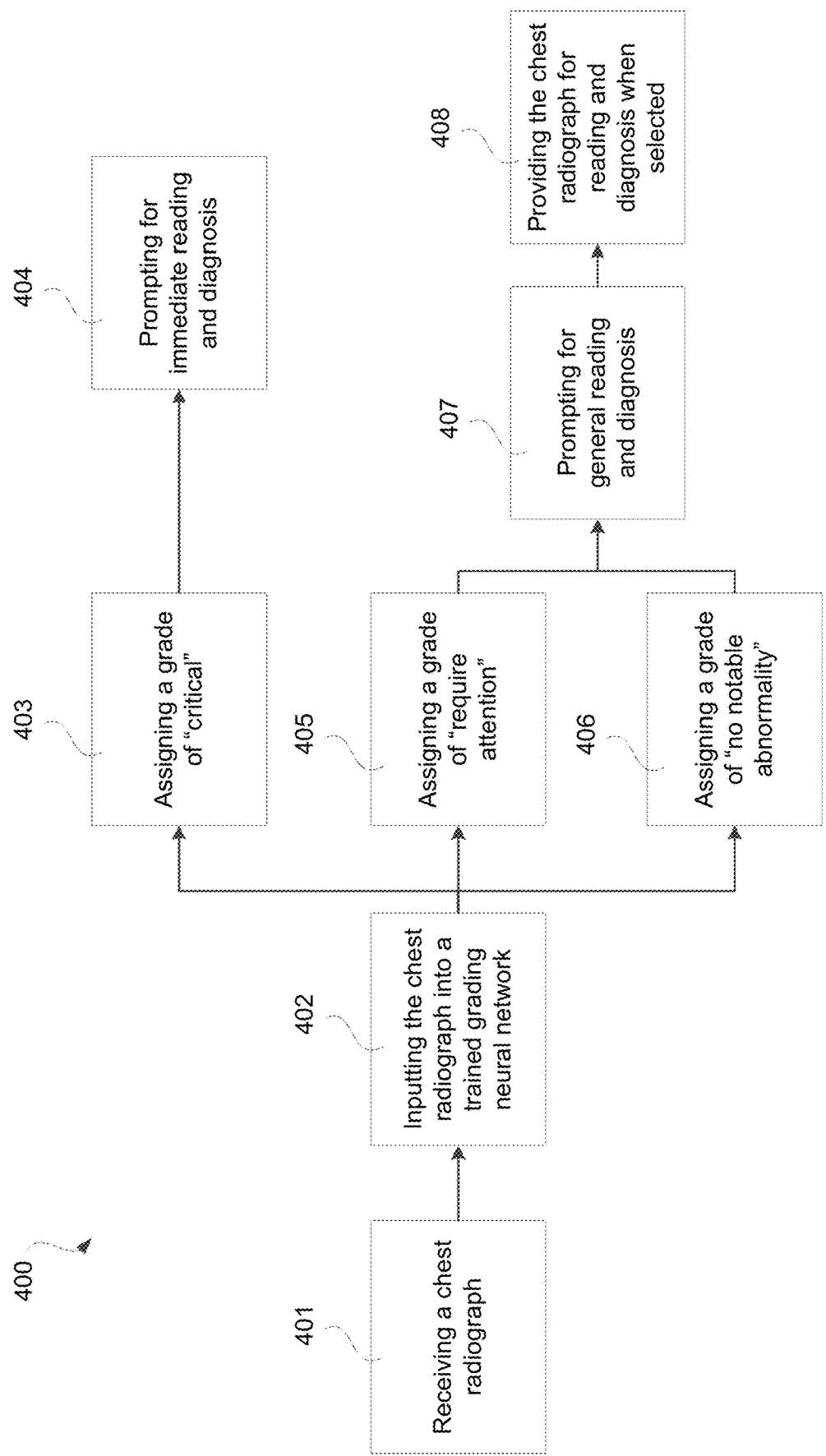
FIG. 4 is a simplified diagram showing a method for grading an X-ray chest radiograph by severity and/or urgency in an emergency or intensive care unit scenario, according to some embodiments of the present invention.

In various embodiments, the intelligent grading of X-ray chest radiographs is applicable to in emergency scenarios such as general outpatient, physical examination, emergency department, and/or intensive care unit. For example, some hospitals implement triage when their emergency resources are limited to maximize the use of medical resources. In yet another example, medical imaging is a frequently used inspection tool in emergency situations and can benefit from increase in efficiency of radiograph-reading workflow, such as via using said intelligent grading of X-ray chest radiographs. FIG. 4, which will be described in more detail, illustrates a method 400 for grading an X-ray chest radiograph in an emergency scenario, in accordance with various embodiments. For example, the method 400 is applicable in intensive care units, such as ones often use bedside X-ray examinations to observe the health status of the patient's chest. In some examples, the method 400 includes determining patients who are unstable and patients who exhibit little status change (e.g., stable). Such application of method 400 can, especially in emergency scenarios, prevent delay treatment such as beyond golden treatment time windows. The application of method 400 can improve treatment results, such as by help prioritizing tasks based on severity and/or urgency graded by an intelligent network (e.g., network 100).

FIG. 4 is a simplified diagram showing a method 400 for grading an X-ray chest radiograph by severity and/or urgency in an emergency or intensive care unit scenario, according to some embodiments of the present invention. This diagram is merely an example, which should not unduly limit the scope of the claims. One of ordinary skill in the art would recognize many variations, alternatives, and modifications. In some examples, the method 400 includes a process 401 of receiving a chest radiograph, a process 402 of inputting the chest radiograph into a trained grading neural network, a process 403 of assigning a grade of "critical" followed by a process 404 of prompting for immediate reading and diagnosis, or a process 405 of assigning a grade of "require attention" or a process 406 of assigning a grade of "no notable abnormality" followed by a process 407 of prompting for general reading and diagnosis and a process 408 of providing the chest radiograph for reading and diagnosis when selected. In various examples, the method 400 is performed by the system 100, such as one trained by system 200, such as one including the lesion identification network described in method 300. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In some examples, the method 400 includes identifying multiple diseases and/or multiple abnormal lesions, outputting a list of lesion candidates and/or one or more corresponding scores. For example, the list of lesion candidates includes a list of lung lesions, a list of heart lesions, a list of cardiovascular lesions, a list of hilar lesions, a list of bone tissue lesions, and/or a list of pleural lesions. In some embodiments, the trained grading neural network (may be referred to as the grading network) is configured to rank, rate, grade, and/or assign a grade to one or more input X-ray chest radiographs, such as based on at least the analysis results of the lesion identification neural network and/or the input X-ray chest radiographs. In some examples, the grading results generated by the grading network include or are based on, for example, the criticality, severity, and/or urgency of the X-ray chest radiographs in whole or partial regions thereof.

In some embodiments, the grading network is configured to assign one of a plurality of grades or labels. For example, the plurality of grades includes critical (or urgent) (e.g., as assigned in process 403), require attention (or attention-needed) (e.g., as assigned in process 405), and no notable abnormality (or no major anomalies) (e.g., as assigned in process 406). In various examples, when the grading result is that the condition of the patient corresponding to the chest radiograph is "critical" (e.g., as assigned in process 403), the method 400 includes performing the process 404 of prompting for immediate reading and diagnosis, such as by a specialist or doctor on staff. In some examples, the method 400 further includes transmitting data to a user (e.g., administrator, expert, etc.). In some examples, when the grading result is that the condition of the patient corresponding to the chest radiograph is "require attention" (e.g., as assigned in process 405) or "no notable abnormality" (e.g., as assigned in process 406), the method 400 includes performing the process 407 of prompting for general reading and diagnosis (e.g., by a radiologist in some later time), and optionally the process 408 of providing the chest radiograph for reading and diagnosis when selected. Similarly, data can be transmitted to a user.

Figure 5:
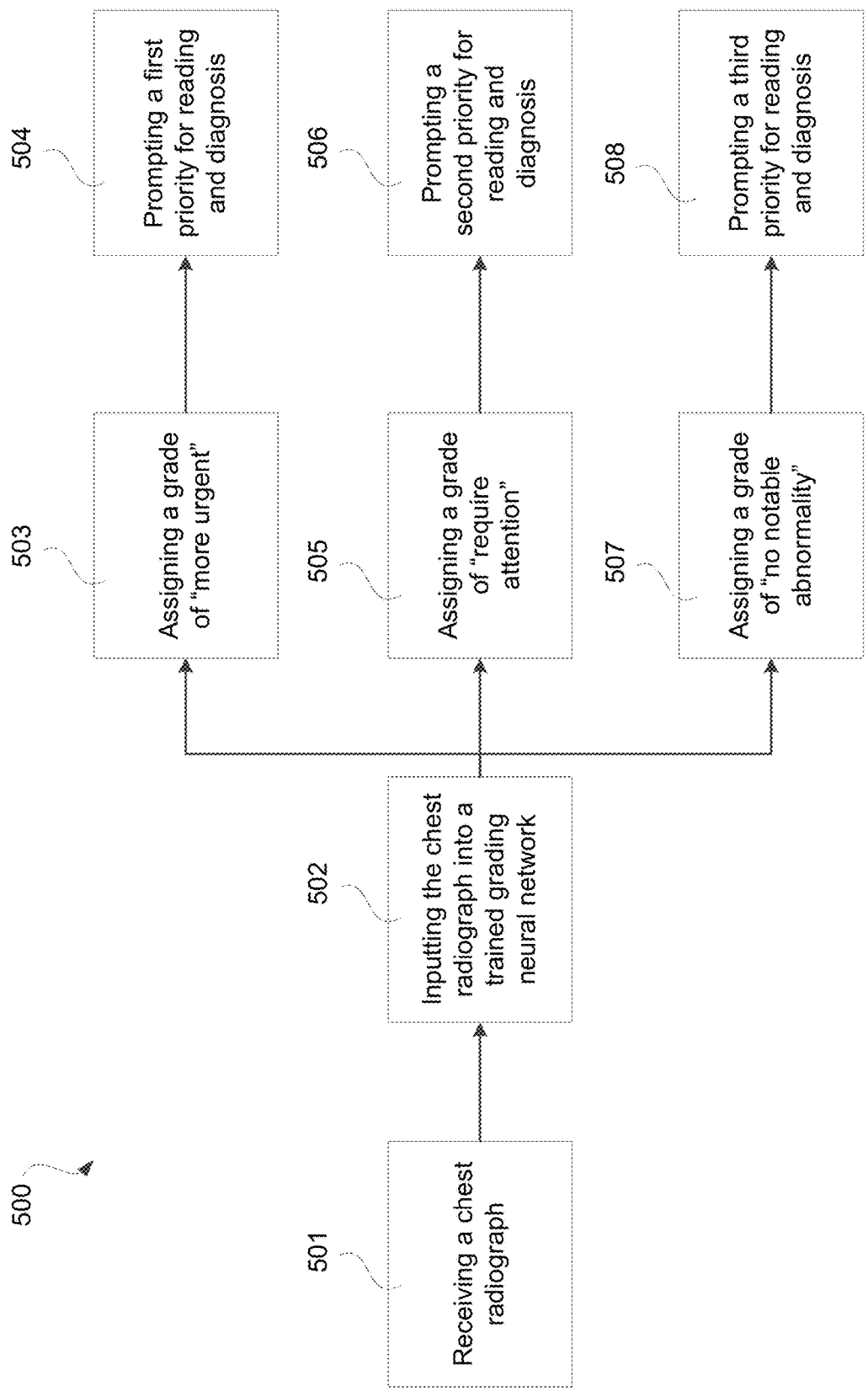
FIG. 5 is a simplified diagram showing a method for grading an X-ray chest radiograph by severity and/or urgency in a physical examination scenario, according to some embodiments of the present invention.

FIG. 5 is a simplified diagram showing a method 500 for grading an X-ray chest radiograph by severity and/or urgency in a physical examination scenario, according to some embodiments of the present invention. This diagram is merely an example, which should not unduly limit the scope of the claims. One of ordinary skill in the art would recognize many variations, alternatives, and modifications. In some examples, the method 500 includes a process 501 of receiving a chest radiograph, a process 502 of inputting the chest radiograph into a trained grading neural network, a process 503 of assigning a grade of "more urgent" followed by a process 504 of prompting a first priority for reading and diagnosis, or a process 505 of assigning a grade of "require attention" followed by a process 506 of prompting a second priority for reading and diagnosis, or a process 507 of assigning a grade of "no notable abnormality" followed by a process 508 of prompting a third priority for reading and diagnosis. In various examples, the method 500 is performed by the system 100, such as one trained by system 200, such as one including the lesion identification network described in method 300. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various embodiments, the method 500 is applicable in scenarios such as physical examinations and in general clinics, which in some examples, use X-ray examinations.

In some examples, the method 500 includes identifying multiple diseases and/or multiple abnormal lesions, outputting a list of lesion candidates and/or one or more corresponding scores. For example, the list of lesion candidates includes a list of lung lesions, a list of heart lesions, a list of cardiovascular lesions, a list of hilar lesions, a list of bone tissue lesions, and/or a list of pleural lesions. In some embodiments, the trained grading neural network (may be referred to as the grading network) is configured to rank, rate, grade, and/or assign a grade to one or more input X-ray chest radiographs, such as based on at least the analysis results of the lesion identification neural network and/or the input X-ray chest radiographs. In some examples, the grading results generated by the grading network include or are based on, for example, the criticality, severity, and/or urgency of the X-ray chest radiographs in whole or partial regions thereof.

In some embodiments, the grading network is configured to assign one of a plurality of grades or labels. For example, the plurality of grades includes critical (or urgent) (e.g., as assigned in process 503), require attention (or attention-needed) (e.g., as assigned in process 505), and no notable abnormality (or no major anomalies) (e.g., as assigned in process 507). In various examples, when the grading result is that the condition of the patient corresponding to the chest radiograph is "critical" (e.g., as assigned in process 503), the method 500 includes performing the process 504 of prompting a first priority for reading and diagnosis, such as by a specialist or doctor on staff. In some examples, when the grading result is that the condition of the patient corresponding to the chest radiograph is "require attention" (e.g., as assigned in process 505), the method 500 includes performing the process 506 of prompting a second priority for reading and diagnosis, such as by the specialist or doctor on staff after reviewing the chest radiographs prompted as having first priority. In certain examples, when the grading result is that the condition of the patient corresponding to the chest radiograph is "no notable abnormality" (e.g., as assigned in process 507), the method 500 includes performing the process 508 of prompting a third priority for reading and diagnosis, such as by the specialist or doctor after reviewing the chest radiographs prompted as having first priority and chest radiographs having second priority. In certain embodiments, the process 508 includes prompting for labor and/or time division for reading and diagnosis of chest radiographs.

In certain examples, the method 400 and/or method 500 includes updating the urgency of the radiology department work list and/or reading and diagnosis priority, such as in real time and/or based on specific situational requirements of the scenario. For example, a situational requirement for some emergency scenarios is for emergency diagnosis and reporting to be completed within thirty minutes of first viewing of the x-ray chest radiograph. In various examples, prioritization of the chest radiographs based on urgency helps automatic division of labor, which in some examples, is based on at least expertise, pay level, and/or seniority (e.g., of each doctor and/or specialist). In some examples, the grading method is customizable appropriately for different applications to support suitable diagnostic workflows.

Figure 6:
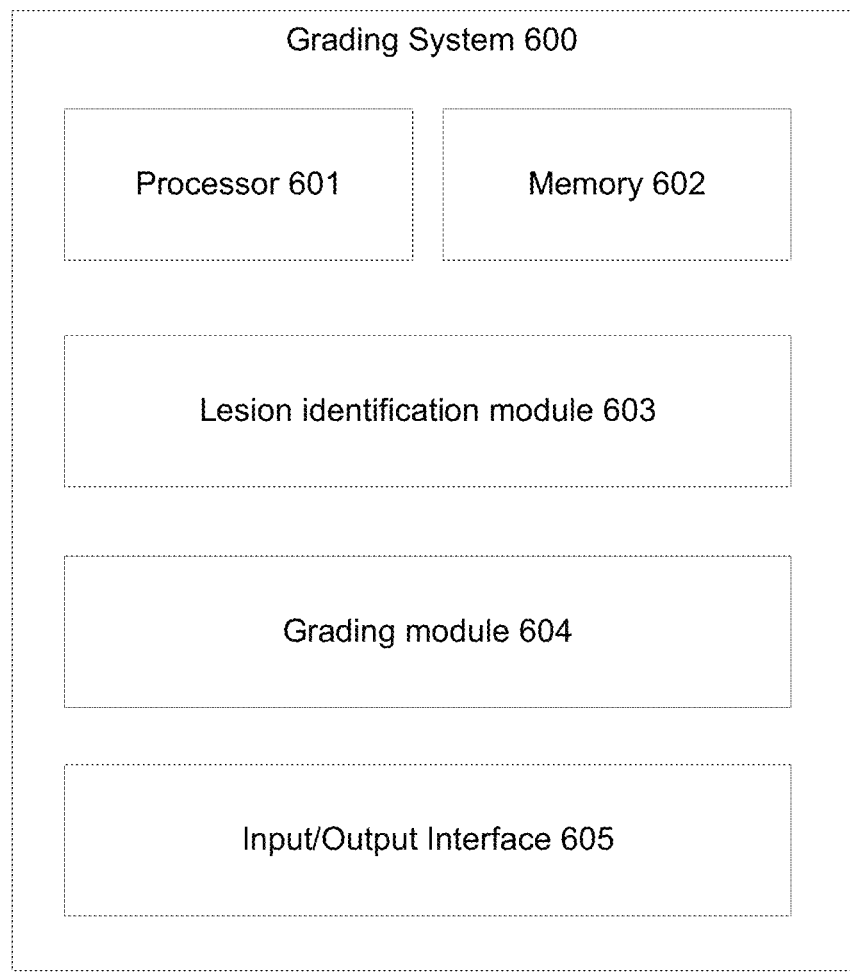
FIG. 6 is a simplified diagram showing a system for grading an X-ray chest radiograph by severity and/or urgency, according to some embodiments of the present invention.

FIG. 6 is a simplified diagram showing a system 600 for grading an X-ray chest radiograph by severity and/or urgency, according to some embodiments of the present invention. This diagram is merely an example, which should not unduly limit the scope of the claims. One of ordinary skill in the art would recognize many variations, alternatives, and modifications. In some examples, the system 600 is configured to perform the method 100, the method 300, the method 400, and/or the method 500. In some examples, the system 600 includes a processor 601, a memory 602, a lesion identification module 603, a grading module 604, and an input/output (I/O) interface 605. Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In some examples, the lesion identification module 603 and/or the grading network module 604 can be implemented in a variety of way, such as be implemented in software or firmware, including software code being stored in memory 602 and executable by processor 601, or in one or more hardware devices including general purpose integrated circuits, dedicated circuits, field programmable gate arrays, and the like. In some examples, the above components are coupled and communicated with each other by, for example, a bus or other mechanism.

In various examples, the input/output interface 605 is configured to receive X-ray chest radiographs and/or to transmit (or pass) data to the lesion identification module 603 and/or the grading module 604 for outputting the classification result. In some embodiments, the lesion identification module 603 is configured to be trained (e.g., machine learning) using training data, and after training, to be used to output a list of lesion candidates and/or corresponding score(s) based on the input chest radiographs. In certain embodiments, the grading module 604 is configured to use the training data for machine learning and, after training, be used to output one or more grading results based on the list of lesion candidates and/or their corresponding score(s) generated by the lesion identification module 603. In some examples, the lesion identification module 603 is a separate (e.g., standalone) module and is not part of the grading system 600.

Figure 7:
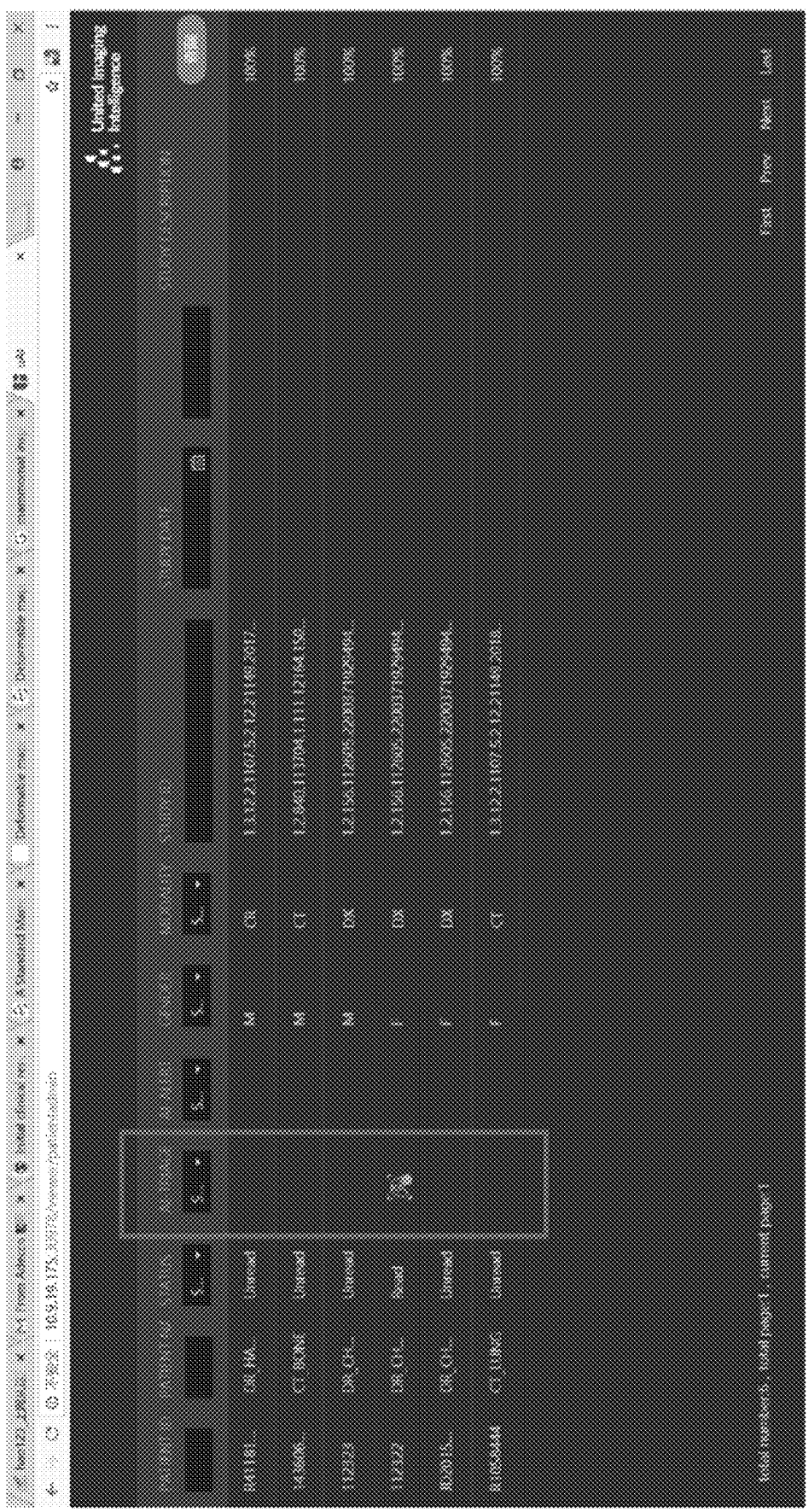
FIG. 7 is an illustrative representation of an interface of a system for grading an X-ray chest radiograph by severity and/or urgency, according to some embodiments of the present invention.

FIG. 7 is an illustrative representation of an interface of a system for grading an X-ray chest radiograph by severity and/or urgency, according to some embodiments of the present invention. As shown, the interface includes an AI-TRIAGE column, where a circular lung icon with an exclamation point (shown in the fourth cell down) represents a chest radiograph require attention (e.g., a problematic chest radiograph), indicating its higher level of concern when compared to the rest of the chest radiographs. In some examples, the icon is prompted for preferential reading and diagnosis for chest radiographs assigned with "critical", "more urgent", or "require attention", such as in method 400 or in method 500. In certain examples, chest radiographs without the icon are ones assigned with a grade of "no notable abnormality" and are prompted for time-divisional and/or labor-divisional reading and diagnosis.

In addition, the term "or" is intended to mean an inclusive "or" rather than an exclusive "or". That is, the phrase "X" employs "A" or "B" to mean any natural collocation, unless otherwise indicated. That is, the phrase "X" using "A" or "B" is satisfied by any of the following examples: X employs A; X employs B; or X employs both A and B. By "connected" and "coupled" are meant to mean the same, meaning the electrical connection of the two devices. In addition, the articles "a", "an" and "the" can be nonlimiting and interpreted as one or more.

Various aspects or features will be presented in the form of a system that can include several devices, components, modules, and the like. It is to be understood and appreciated that the various systems may include additional devices, components, modules, etc. and/or may not include all of the devices, components, modules, etc. discussed in connection with the Figures. A combination of these methods can also be used.

Various illustrative logic, logic blocks, modules, and circuits described in connection with the embodiments disclosed herein may be used in general purpose processors, digital signal processors (DSPs), application specific integrated circuits (ASICs), field programmable gate arrays (FPGAs). Or other programmable logic devices, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor may also be implemented as a combination of computing devices, such as a combination of a DSP and a microprocessor, a plurality of microprocessors, one or more microprocessors in conjunction with a DSP core, or any other such configuration. Furthermore, at least one processor can include one or more modules operable to perform one or more of the steps and/or actions described above. For example, the embodiments described above in connection with various methods can be implemented by a processor and a memory coupled to the processor, where the processor can be configured to perform any of the steps of any of the methods described above, or any combination thereof.

Furthermore, the steps and/or actions of a method or algorithm described in connection with the aspects disclosed herein can be implemented directly in hardware, in a software module executed by a processor, or in a combination of the two. For example, the embodiments described above in connection with the various methods can be implemented by a computer readable medium storing computer program code, which when executed by a processor/computer performs any of the steps of any of the methods described above, or any combination thereof.

In various embodiments, a system for grading a medical image includes a grading network configured to provide a grading result corresponding to the medical image based on at least the medical image and/or a list of lesion candidates generated by a lesion identification network. In some examples, the system is implemented according to at least the grading system 600 of FIG. 6 and/or configured to perform at least the method 100 of FIG. 1, the method 300 of FIG. 3A, the method 400 of FIG. 4, and/or the method 500 of FIG. 5.

In some embodiments, the grading network is further configured to provide the grading result corresponding to the medical image based on at least the medical image and the list of lesion candidates generated by the lesion identification network.

In some embodiments, the grading network is further configured to provide the grading result corresponding to the medical image based on at least the medical image.

In some embodiments, the lesion identification network is configured to provide a score corresponding to the list of lesion candidates. In some examples, the grading result is provided further based on the score. In certain examples, the score is provided based on at least a probability value corresponding to the medical image including lesions of multiple lesion categories.

In some embodiments, the medical image includes a chest radiograph. In some examples, the list of lesion candidates includes at least one list selected from a group consisting of a list of lung lesion candidates, a list of cardiac lesion candidates, a list of cardiovascular lesion candidates, a list of hilar lesion candidates, a list of bone tissue lesion candidates, and a list of pleural lesion candidates.

In some embodiments, the grading network is further configured to provide one or more outputs to guide manual scheduling of a plurality of radiographs for manual review and diagnosis based on at least a plurality of grading results corresponding to the plurality of radiographs. In some examples, the grading network is further configured to automatically schedule the plurality of radiographs for manual review and diagnosis based on at least a plurality of grading results corresponding to the plurality of radiographs.

In some embodiments, the grading network is further configured to provide one or more outputs to guide manual scheduling of a plurality of radiographs for manual review and diagnosis based on at least a plurality of grading results corresponding to the plurality of radiographs, and automatically schedule the plurality of radiographs for manual review and diagnosis based on at least a plurality of grading results corresponding to the plurality of radiographs.

In some embodiments, the grading network is a student network trained by an attention transfer learning process includes: establishing a teacher network and the student network for the grading network; training the teacher network; and training the student network based on at least: extracting a feature map from one or more middle layers corresponding to both the student network and the teacher network; calculating one or more attention transfer learning losses corresponding to the one or more middle layers; and backpropagating the one or more attention transfer learning losses into the student network.

In some embodiments, the grading result corresponds to at least one selected from a group consisting of severity and urgency.

In some embodiments, the lesion identification network is configured to identify at least one lesion characteristic selected from a group consisting of color, shape, size, grayscale value, position, and morphology.

In some embodiments, the grading result is provided based on the medical image as a whole or one or more partial regions of the medical image.

In some embodiments, the grading result is selected from a group consisting of a first grade, a second grade, and a third grade, wherein: the first grade corresponds to a first priority for reading and diagnosis; the second grade corresponds to a second priority for reading and diagnosis; the third grade corresponds to a third priority for reading and diagnosis; the first priority being greater than the second and third priorities.

In various embodiments, a computer-implemented method for grading a medical image includes providing a grading result corresponding to the medical image based on at least the medical image and/or a list of lesion candidates generated by a lesion identification network. In some examples, the method is implemented according to at least the method 100 of FIG. 1, the method 300 of FIG. 3A, the method 400 of FIG. 4, and/or the method 500 of FIG. 5. In certain examples, the method is implemented by at least the grading system 600 of FIG. 6.

In some embodiments, the computer-implemented method further includes providing the grading result corresponding to the medical image based on at least the medical image and the list of lesion candidates generated by the lesion identification network.

In some embodiments, the computer-implemented method further includes providing the grading result corresponding to the medical image based on at least the medical image.

In some embodiments, the computer-implemented method further includes providing a score corresponding to the list of lesion candidates using the lesion identification network. In some examples, the providing a grading result is further based on the score. In certain examples, the providing a score is based on at least a probability value corresponding to the medical image including lesions of multiple lesion categories.

In some embodiments, the computer-implemented method further includes providing one or more outputs to guide manual scheduling of a plurality of radiographs for manual review and diagnosis based on at least a plurality of grading results corresponding to the plurality of radiographs. In some examples, the computer-implemented method further includes automatically scheduling the plurality of radiographs for manual review and diagnosis based on at least a plurality of grading results corresponding to the plurality of radiographs.

In some embodiments, the computer-implemented method further includes training a student network to be the grading network based on an attention transfer learning process including: establishing a teacher network and the student network for the grading network; training the teacher network; and training the student network based on at least: extracting a feature map from one or more middle layers corresponding to both the student network and the teacher network; calculating one or more attention transfer learning losses corresponding to the one or more middle layers; and backpropagating the one or more attention transfer learning losses into the student network.

In some embodiments, scheduling of the plurality of radiographs for manual review and diagnosis is based on at least one selected from a group consisting of expertise, pay level, and seniority.

In various embodiments, a non-transitory computer-readable medium with instructions stored thereon, that when executed by a processor, perform the process of: providing a grading result corresponding to the medical image based on at least the medical image and/or a list of lesion candidates generated by a lesion identification network. In some examples, the non-transitory computer-readable medium with instructions stored thereon is implemented according to at least the method 100 of FIG. 1, and/or a computer (e.g., a terminal).

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A system for grading a medical image, the system comprising:
    a grading network configured to provide a grading result corresponding to the medical image based on at least the medical image and/or a list of lesion candidates generated by a lesion identification network;
    wherein the grading network is further configured to at least one of:
        provide one or more outputs to guide manual scheduling of a plurality of radiographs for manual review and diagnosis based on at least a plurality of grading results corresponding to the plurality of radiographs; or
        automatically schedule the plurality of radiographs for manual review and diagnosis based on at least a plurality of grading results corresponding to the plurality of radiographs.

2. The system of claim 1, wherein:
    the grading network is further configured to provide the grading result corresponding to the medical image based on at least the medical image and the list of lesion candidates generated by the lesion identification network.

3. The system of claim 1, wherein:
    the grading network is further configured to provide the grading result corresponding to the medical image based on at least the medical image.

4. The system of claim 1, wherein:
    the lesion identification network is configured to provide a score corresponding to the list of lesion candidates;
    the grading result is provided further based on the score; and
    the score is provided based on at least a probability value corresponding to the medical image including lesions of multiple lesion categories.

5. The system of claim 1, wherein:
    the medical image includes a chest radiograph; and
    the list of lesion candidates includes at least one list selected from a group consisting of a list of lung lesion candidates, a list of cardiac lesion candidates, a list of cardiovascular lesion candidates, a list of hilar lesion candidates, a list of bone tissue lesion candidates, and a list of pleural lesion candidates.

6. The system of claim 1, wherein the grading network is a student network trained by an attention transfer learning process comprising:
   establishing a teacher network and the student network for the grading network;
   training the teacher network; and
   training the student network based on at least:
      extracting a feature map from one or more middle layers corresponding to both the student network and the teacher network;
      calculating one or more attention transfer learning losses corresponding to the one or more middle layers; and
      backpropagating the one or more attention transfer learning losses into the student network.

7. The system of claim 1, wherein the grading result corresponds to at least one selected from a group consisting of severity and urgency.

8. The system of claim 1, wherein the lesion identification network is configured to identify at least one lesion characteristic selected from a group consisting of color, shape, size, grayscale value, position, and morphology.

9. The system of claim 1, wherein the grading result is provided based on the medical image as a whole or one or more partial regions of the medical image.

10. The system of claim 1, wherein the grading result is selected from a group consisting of a first grade, a second grade, and a third grade, wherein:
   the first grade corresponds to a first priority for reading and diagnosis;
   the second grade corresponds to a second priority for reading and diagnosis;
   the third grade corresponds to a third priority for reading and diagnosis;
   the first priority being greater than the second and third priorities.

11. A computer-implemented method for grading a medical image, the method comprising:
   providing a grading result corresponding to the medical image based on at least the medical image and/or a list of lesion candidates generated by a lesion identification network; and at least one of:
      providing one or more outputs to guide manual scheduling of a plurality of radiographs for manual review and diagnosis based on at least a plurality of grading results corresponding to the plurality of radiographs; or
      automatically scheduling the plurality of radiographs for manual review and diagnosis based on at least a plurality of grading results corresponding to the plurality of radiographs.

12. The computer-implemented method of claim 11, further including:
   providing the grading result corresponding to the medical image based on at least the medical image and the list of lesion candidates generated by the lesion identification network.

13. The computer-implemented method of claim 11, further including:
   providing the grading result corresponding to the medical image based on at least the medical image.

14. The computer-implemented method of claim 11, further includes:
   providing a score corresponding to the list of lesion candidates using the lesion identification network;
   wherein the providing a grading result is further based on the score; and
   wherein the providing a score is based on at least a probability value corresponding to the medical image including lesions of multiple lesion categories.

15. The computer-implemented method of claim 11, further includes training a student network to be the grading network based on an attention transfer learning process comprising:
   establishing a teacher network and the student network for the grading network;
   training the teacher network; and
   training the student network based on at least:
      extracting a feature map from one or more middle layers corresponding to both the student network and the teacher network;
      calculating one or more attention transfer learning losses corresponding to the one or more middle layers; and
      backpropagating the one or more attention transfer learning losses into the student network.

16. The computer-implemented method of claim 11, wherein the scheduling of the plurality of radiographs for manual review and diagnosis is based on at least one selected from a group consisting of expertise, pay level, and seniority.

17. A non-transitory computer-readable medium with instructions stored thereon, that when executed by a processor, perform the processes of:
   providing a grading result corresponding to the medical image based on at least the medical image and/or a list of lesion candidates generated by a lesion identification network; and at least one of:
      providing one or more outputs to guide manual scheduling of a plurality of radiographs for manual review and diagnosis based on at least a plurality of grading results corresponding to the plurality of radiographs; or
      automatically scheduling the plurality of radiographs for manual review and diagnosis based on at least a plurality of grading results corresponding to the plurality of radiographs.

* * * * *